United States Patent [19]
Swanson

[11] Patent Number: 5,344,447
[45] Date of Patent: Sep. 6, 1994

[54] DIFFRACTIVE TRIFOCAL INTRA-OCULAR LENS DESIGN

[75] Inventor: Gary J. Swanson, Lexington, Mass.

[73] Assignee: Massachusetts Institute of Technology, Cambridge, Miss.

[21] Appl. No.: 975,511

[22] Filed: Nov. 12, 1992

[51] Int. Cl.$^5$ .......................... A61F 2/16; G02C 7/04
[52] U.S. Cl. ........................................ 623/6; 351/161
[58] Field of Search .......................... 351/161; 623/4–6

[56] References Cited

U.S. PATENT DOCUMENTS

| | | |
|---|---|---|
| 4,210,391 | 7/1980 | Cohen . |
| 4,637,697 | 1/1987 | Freeman . |
| 4,881,805 | 11/1989 | Cohen . |
| 4,995,714 | 2/1991 | Cohen . |
| 4,995,715 | 2/1991 | Cohen . |
| 5,016,977 | 5/1991 | Baude et al. ........................ 623/6 X |
| 5,056,908 | 10/1991 | Cohen ................................. 623/6 X |
| 5,071,207 | 12/1991 | Ceglio et al. . |
| 5,076,684 | 12/1991 | Simpson et al. . |
| 5,089,023 | 2/1992 | Swanson . |
| 5,096,285 | 3/1992 | Silberman . |
| 5,116,111 | 5/1992 | Simpson et al. . |
| 5,121,979 | 6/1992 | Cohen . |
| 5,121,980 | 6/1992 | Cohen . |
| 5,129,718 | 7/1992 | Futhey et al. . |
| 5,178,636 | 1/1993 | Silberman .............................. 623/6 |

*Primary Examiner*—Randall L. Green
*Assistant Examiner*—Mary Beth Jones
*Attorney, Agent, or Firm*—Choate, Hall & Stewart

[57] ABSTRACT

An intraocular lens including a refractive/diffractive lens having an anterior surface and a posterior surface and a generally anterior posterior optical axis. At least one of the surfaces has a diffractive lens profile that is binary in phase, and produces three useful focal points. The diffractive lens profile is designed to provide three foci each containing 28.8% of the incident light, with the residual 14% of the light going into other foci. Additionally, some of the out-of-focus light of this design contributes positively to the image, and the resultant maximum image contrast is above 28.8%. This design adds clear mid-range vision, at the expense of a slight decrease in near and far vision, and the added mid-range vision makes the device less sensitive to longitudinal placement in the eye.

4 Claims, 6 Drawing Sheets

DIFFRACTIVE TRIFOCAL INTRA-OCULAR LENS DESIGN

BACKGROUND OF THE INVENTION

This invention relates to refractive/diffractive intra-ocular lenses having a plurality of focal lengths.

Intra-ocular lenses ("IOL's") are routinely used as replacements for cataract impaired natural lenses. An ophthalmic surgeon removes the damaged natural lens and implants the artificial IOL. An IOL is simply a plastic lens that has the same optical power as the natural lens that it replaces. The main difference between the natural lens and an IOL is the inability of an IOL to change its focal length. The natural lens is pliable, and its shape is controlled by muscles in the eye. The change in shape of the lens causes a change in the focal length of the lens. The natural eye is therefore able to focus over a range of distances, from approximately 15 inches to infinity. As perceived by the eye an object is at a distance of infinity if it is about 12 feet or further away. The IOL's shape, on the other hand, is fixed, and can't be changed by muscles in the eye. Consequently, the resulting focal length of the IOL is also fixed. An eye that has an IOL is, therefore, no longer able to accommodate its focus. In the majority of cases, the IOL recipient must wear bifocal eyeglasses in order to see clearly at both near and far distances.

Numerous designs of IOL's have been developed in order to provide more than one focal length. The multi-focal designs can be classified into two groups, either completely refractive or refractive/diffractive. In either case, the incident light is split in such a way that a certain percentage of light is focused at different distances. Refractive/diffractive designs have the advantage over refractive designs in that they can be designed to be insensitive to decentration in the eye as well as to the pupil size of the eye.

It should be stressed that the image quality of a multi-focal IOL suffers from a loss of contrast. The fraction of the light that is not in-focus for a particular image distance contributes to a background bias. For example, consider a bifocal IOL that has been designed to produce two foci, with 50% of the incident light focused in each one. At either foci 50% of the light will produce an out-of focus image, that is perceived by the eye as an approximately constant background bias, resulting in an image contrast of about 50%. Ideally, one would like to have an IOL that could produce focused images at many different distances, yet this can result in an increase in image bias as a function of the number of focal points. For example, an IOL with ten focal points, each containing 10% of the incident light, would result in a maximum image contrast of around 10%. Thus there exists a point where the advantages of having a number of foci are negated by the loss of image contrast. Fortunately, depending upon the parameters of the IOL, some of the out-of-focus light can contribute positively to the image. The exact contrast of the image can be determined by quantitative analysis.

Quantitatively, the image contrast is expressed by the modulation transfer function ("MTF") of the IOL. The MTF can be used to determine what the contrast will be for any given image distance and spatial frequency. The MTF by itself is not enough information to determine whether or not a design would be acceptable as an IOL. The visual factors, both physiological and psychological, play a large part in determining the acceptability of an image.

U.S. Pat Nos. 4,210,391; 4,995,714; 4,995,715; 5,121,980; 5,121,979; and 5,129,718, all issued to Cohen ("Cohen Patents"), teach the use of a phase zone plate having a plurality of annular regions that direct light to two foci and rely upon simultaneous vision to discard unfocused images. They disclose the use of alternating concentric Fresnel zones having a generally saw-toothed design to diffract the incident light such that two focal points are produced in the $0^{th}$ and $1^{st}$ order each of which contains about 40% of the incident light. Thus, at either of the image locations for which the IOL was designed, 40% of the light will produce a focused image, 40% of the light will produce an out-of-focus image, and the remainder of the light goes into other focal points. The out-of focus image will be perceived by the eye as an approximately constant background bias, resulting in an image contrast of about 40%.

U.S. Pat. Nos. 5,076,684; 5,116,111; and 5,129,718, issued to Simpson et al., Simpson et al., and Furhey et al., teach a refractive/diffractive bifocal ophthalmic lens having a phase zone plate embedded within the lens such that the anterior and posterior surfaces of the lens are smooth. The diffractive zone is of a generally saw-toothed or stepped design, and the zones are not of equal area. For instance the central zone is made smaller than the other zones in order to ensure adequate functioning of the lens in a plurality of light conditions.

A "phase zone plate", as used herein, is a unitary optical region of a lens utilizing the combination of a zone plate and optical facets to produce a specific wavefront which results in a specific intensity distribution of light at the various order foci of the zone plate.

At present, only one multi-focal IOL has been approved for use by the FDA. The IOL, based on U.S. Pat. No. 4,637,697 issued to Freeman and produced by Minnesota Mining and Manufacturing Company ("3M"), is a refractive/diffractive bifocal design. The diffractive surface profile is made such that it produces two focal points each containing 40% of the incident light. The residual 20% of the light goes into other focal points, and essentially results in an additional image bias. Therefore, each of the two useful foci form images with a maximum contrast of 40%. The important point is that this design, with a 40% maximum contrast, has been tested in vivo, and found to be acceptable. The MTF of the 3M design can be used as a baseline to evaluate the potential acceptability of other designs.

SUMMARY OF THE INVENTION

The invention features, in one aspect an intraocular lens that includes a refractive/diffractive lens having a diffractive lens profile that is binary in phase, and produces three useful focal points. A "diffractive lens profile", as used herein, means an optical surface that focuses light by diffraction. This diffractive lens profile is designed to provide three foci each containing 28.8% of the incident light, with the residual 14% of the light going into other foci. Additionally, some of the out-of-focus light of this design contributes positively to the image, and the resultant maximum image contrast is above 28.8%. This design adds clear mid-range vision, at the expense of a slight decrease in near and far vision, and the added midrange vision makes the device less sensitive to longitudinal placement in the eye.

In preferred embodiments, at least one surface of the binary phase refractive/diffractive lens is generally planar. The diffractive profile is formed on the generally planar surface of the lens, and the diffractive lens profile is circular with its center in the optical axis of the lens.

In preferred embodiments the diffractive lens profile is binary in phase, with a phase depth of 0.3196 waves at the center wavelength. Preferably, the profile has an optimal depth D given by $$D = \frac{0.32\lambda_0}{\Delta n}$$

where $\lambda_0$ is about 550 nm, and $\Delta n$ is the difference between the index of refraction of the lens and the index of refraction of the aqueous humor. Preferably the radial transition locations "$r_m$" are $$r_m = \sqrt{\frac{m\lambda_0}{P}}$$

where m is 0, 1, 2, 3, ..., and P is the power of the diffractive element in diopters.

DESCRIPTION OF THE PREFERRED EMBODIMENTS

Trifocal Diffractive Lens

Figure 1:
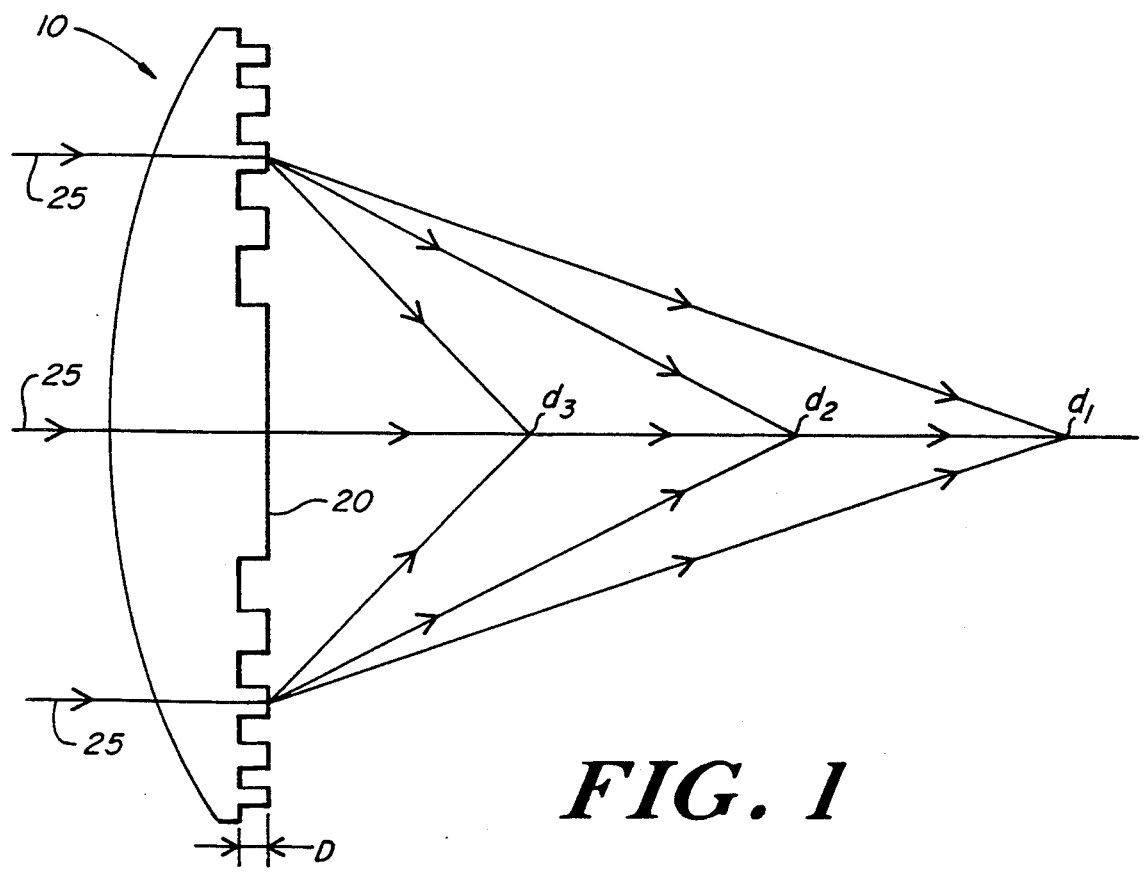
FIG. 1 is an exaggerated diagram of a section through the optical axis of an intraocular implant having a binary profile according to the invention. D is the depth of the diffractive phase zone plate. $d_1$, $d_2$, and $d_3$ are representative of the three focal points generated by the lens for far, mid-range, and near vision, respectively.

With reference now to FIG. 1, refractive/diffractive lens 10 is shown having a generally convex-planar configuration and having a diffractive lens profile 20 that is binary in phase on its posterior surface. Although the drawing shows only five zones, more typically 20-30 zones would be provided. The exact number of zones would depend on the amount of change from the base optical power of the lens, the size of the lens and the design wavelength, among other factors. Such a refractive/diffractive lens can have three focal lengths. Light of wavelength $\lambda_0$ that is emitted as shown for example in FIG. 1 by rays 25 from a distant object, and incident on lens 10 having a focal power P, is focused at distance $d_1$, $d_2$, and $d_3$. The design of the lens is discussed further below.

Figure 2:
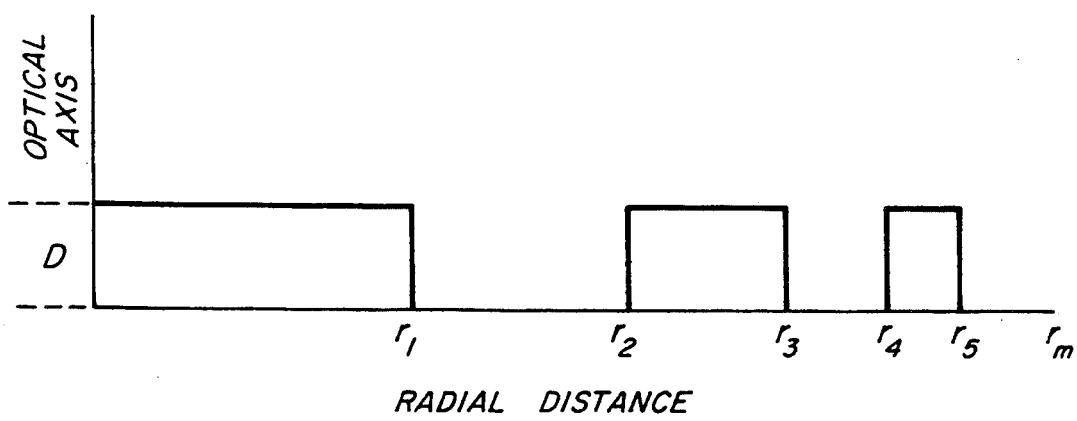
FIG. 2 is an exaggerated diagram of the radial transition locations according to the invention. D is the depth of the diffractive phase zone plate, and $r_1$, $r_2$, $r_3$, ..., $r_m$ are the positions of the radial transition locations.

The lens body of an intraocular lens implant for human use, for example, is typically about 5–7 mm in diameter. The optimal depth D for a trifocal lens is given by the equation $$D = \frac{0.32\lambda_0}{\Delta n}$$

where $\lambda_0$ is about 550 nm, and $\Delta n$ is the difference between the index of refraction of the lens and the index of refraction of the aqueous humor. This gives an optimal phase depth of 0.3196 waves at the center wavelength. With reference now to FIG. 2, an exaggerated view of the radial transition locations, $r_1$, $r_2$, $r_3$, ..., $r_m$ are shown. The radial transition locations can be calculated with the equation $$r_m = \sqrt{\frac{m\lambda_0}{P}}$$

where $\lambda_0$ is about 550 nm, m is 0, 1, 2, 3, ..., and P is the power of the diffractive element in diopters.

The three focal points of the lens are achieved by designing the refractive component of the trifocal lens to focus clearly for the mid-range. The refractive power needed to focus the eye clearly for far vision, "$P_r^\infty$", is about 20 diopters, this is augmented with an additional refractive power, "$P_r$", that is needed to focus the eye for mid-range vision. The diffractive power, "P", of the lens provides the power needed to clearly focus the eye for near vision. Thus, the refractive/diffractive lens has three different powers; $(P_r^\infty + P_r) - P$ that gives far vision, $(P_r^\infty + P_r)$ that gives mid-range vision, and $(P_r^\infty + P_r) + P$ that gives near vision. The corresponding distances, in meters, at which the eye is in focus can be calculated by $1/(P_r - P)$ for the far vision, $1/P_r$ for the mid-range vision, and $1/(P_r + P)$ for the near vision.

For example, if $P_r$ is chosen to be 1.5 diopters, and P is chosen to be 1.5 diopters, then the three focal points produced by the lens would be for distances of infinity (about 4 meters and further), 67 cm, and 33 cm.

Comparison of the Trifocal lens with the 3M lens

Figure 3:
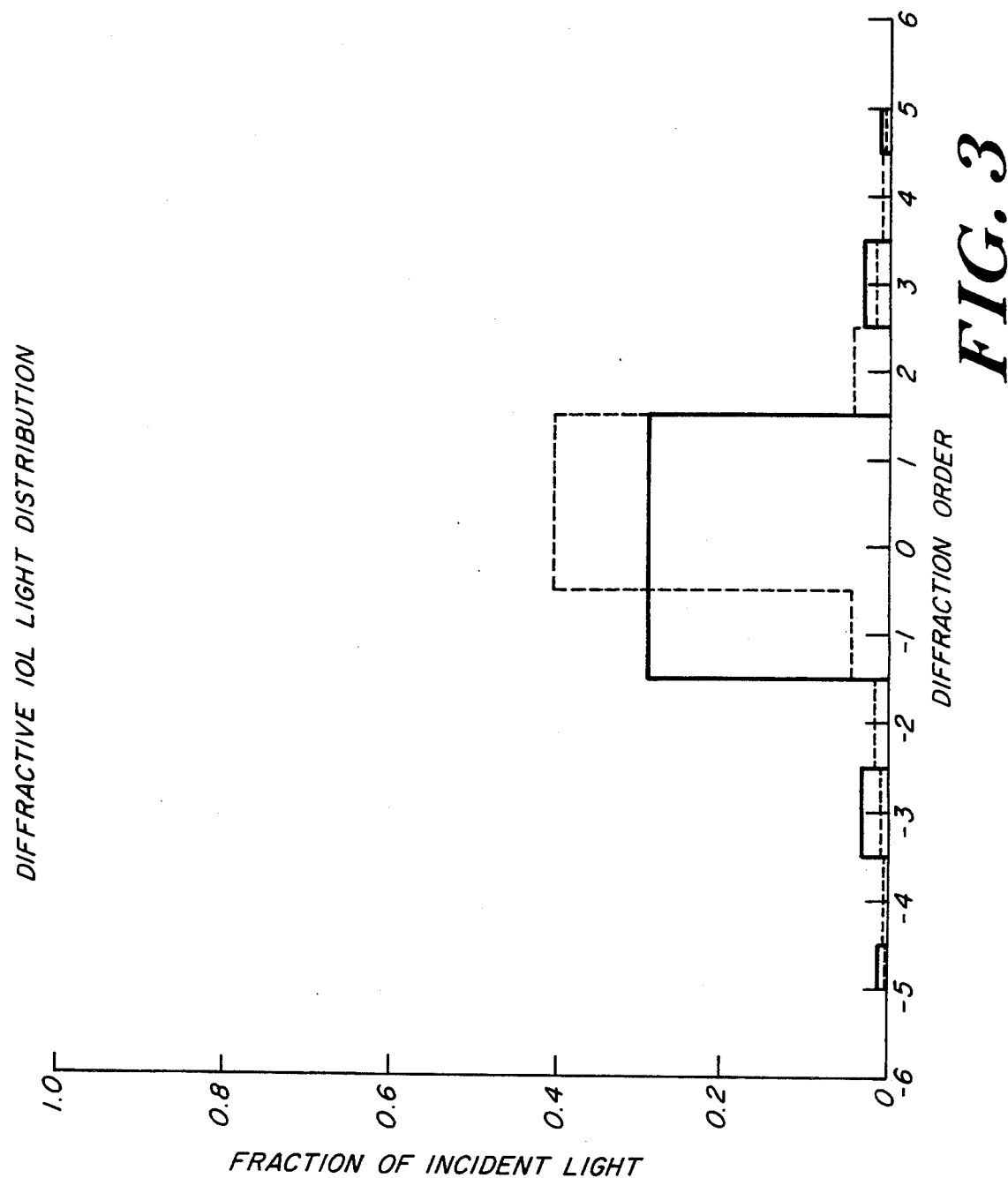
FIG. 3 is a graph of the distribution of light for the trifocal IOL (solid line) as compared to the 3M IOL (dotted line).

The fraction of the incident light going into each diffraction order (i.e. focal point) is shown in FIG. 3. The solid line is for the trifocal design. The dotted line shows, for comparison, the light distribution of the 3M design. Notice that the 3M design utilizes the zero and first diffraction orders for the two focal points. The trifocal design of this invention utilizes the zero and ±first orders. In the 3M design, near vision is produced by the first order and distant vision by the zero order. In the trifocal design, near vision is produced by the first order, distant vision by the negative first order, and mid-range vision by the zero order.

The refractive component of the 3M bifocal IOL has the proper optical power, approximately 20 diopters, so that it focuses clearly for distant vision. The additional optical power needed to focus between the near and far limits of normal vision is approximately 3.5 diopters. The 3M design is a diffractive lens profile having an optical power of 3.5 diopters. Therefore, the zero order of the diffractive lens, along with the refractive lens, focuses for far vision. The first order of the diffractive lens (having 3.5 diopters of optical power), along with the refractive component, focuses for near vision.

The trifocal design is different from the 3M design in that the refractive component alone is designed to focus clearly for the mid-range. The negative first order of the diffractive lens along with the refractive component, will focus clearly for distant objects, and the positive first order of the diffractive lens combined with the refractive lens results in an element that focuses clearly for near vision.

It is important to note that the feature sizes of a diffractive lens are inversely proportional to the optical power of the test order. "Feature size", as used herein, is the spacing between the radial transitions. Since the first order of the trifocal design has half the optical power of the 3M design and the feature sizes of a diffractive lens are inversely proportional to the optical power of the first order, the feature sizes of the trifocal design are twice as large as the 3M design. Furthermore, the trifocal design has only binary features, making the fabrication with binary optics technology extremely easy.

Another major difference between the trifocal design of the invention and the 3M design is the profile depth. The 3M design has an optical path difference ("OPD") depth of 0.5 waves. The trifocal design has an OPD depth of only 0.3196 waves, or one third less than the depth of the 3M design, resulting in a decrease in the amount of debris likely to be trapped in the grooves.

Computer Simulation of Trifocal Design

A computer program was written to simulate the optical performance of the trifocal design. The performance criterion is the modulation transfer function (MTF). The program also calculates the performance of the 3M design, so that it can be used for comparison purposes.

Figure 4:
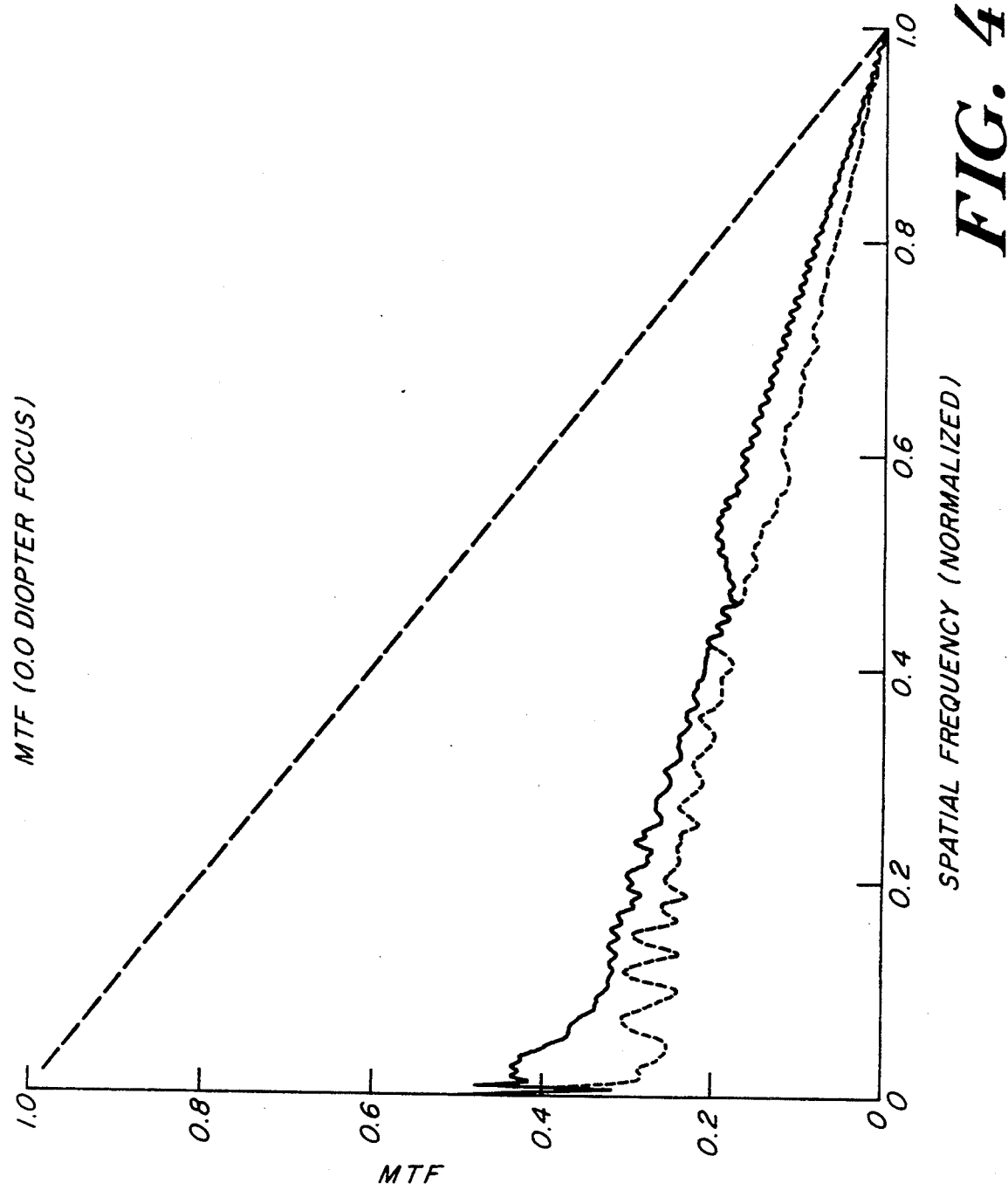
FIG. 4 is a plot of the MTF of the image contrast versus spatial frequency for far vision. A comparison is shown of the trifocal IOL of the invention (dotted line), the 3M design (solid line) and a perfect lens (dashed line).
Figure 5:
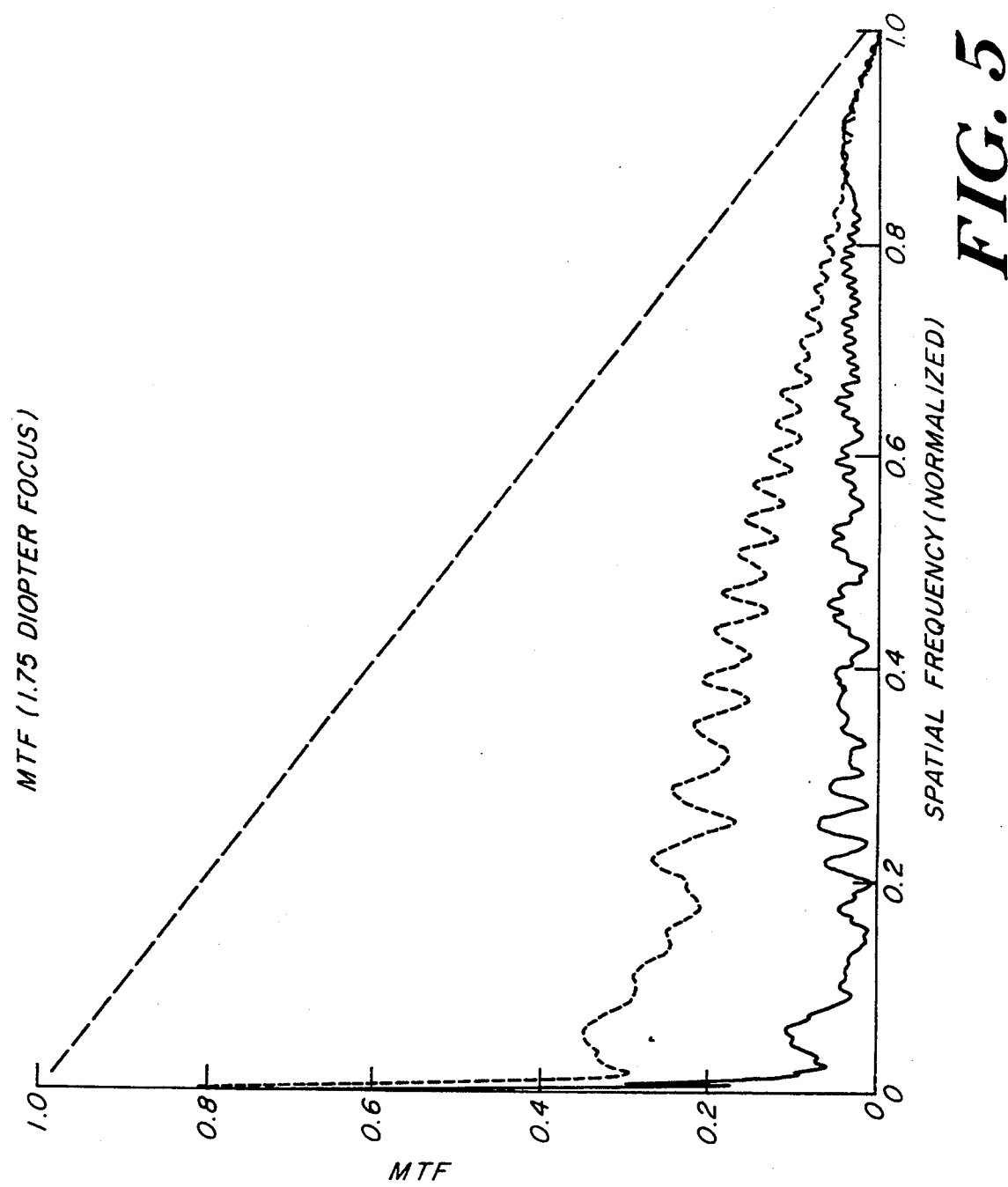
FIG. 5 is a plot of the MTF of the image contrast versus spatial frequency for mid-range vision. A comparison is shown of the trifocal IOL of the invention (dotted line), the 3M design (solid line) and a perfect lens (dashed line).
Figure 6:
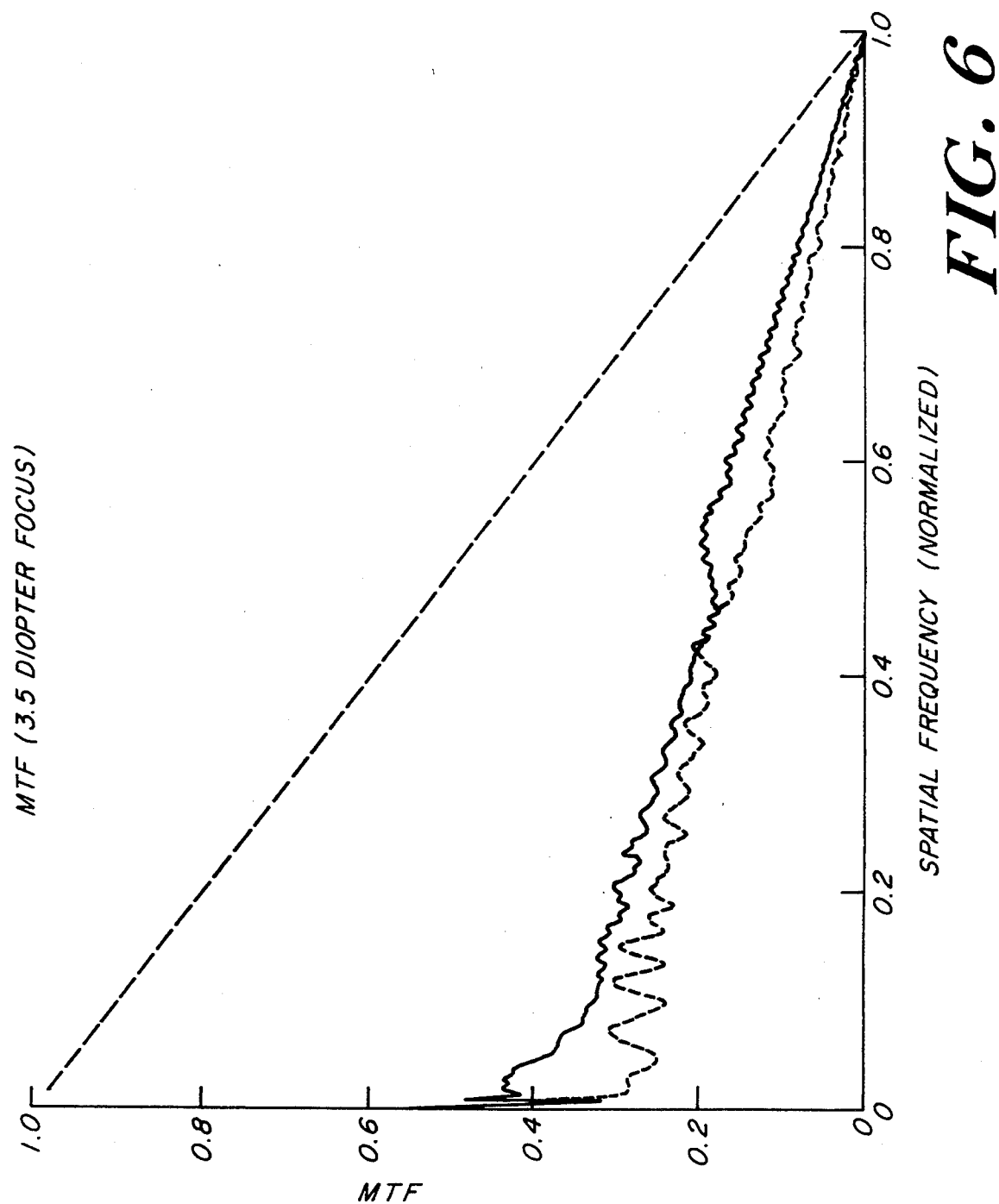
FIG. 6 is a plot of the MTF of the image contrast versus spatial frequency for near vision. A comparison is shown of the trifocal IOL of the invention (dotted line), the 3M design (solid line) and a perfect lens (dashed line).

The results of the computer simulation are shown in FIGS. 4, 5, and 6. These figures are MTF plots of the image contrast versus spatial frequency for far, mid-range, and near vision, respectively. The solid line is for the 3M design, the dotted line is for the trifocal design, and the dashed line represents a perfect lens (i.e. diffraction limited resolution). Notice in FIGS. 4 and 6 that the MTF performance of the 3M design and the trifocal design for far and near range vision is very close, with the 3M performance slightly better. The mid-range vision, shown in FIG. 5, is dramatically different for the two designs. The trifocal design performs as well at mid-range distances as it does at near and far distances. The 3M design, however, has very poor performance at the mid-range.

Figure 7:
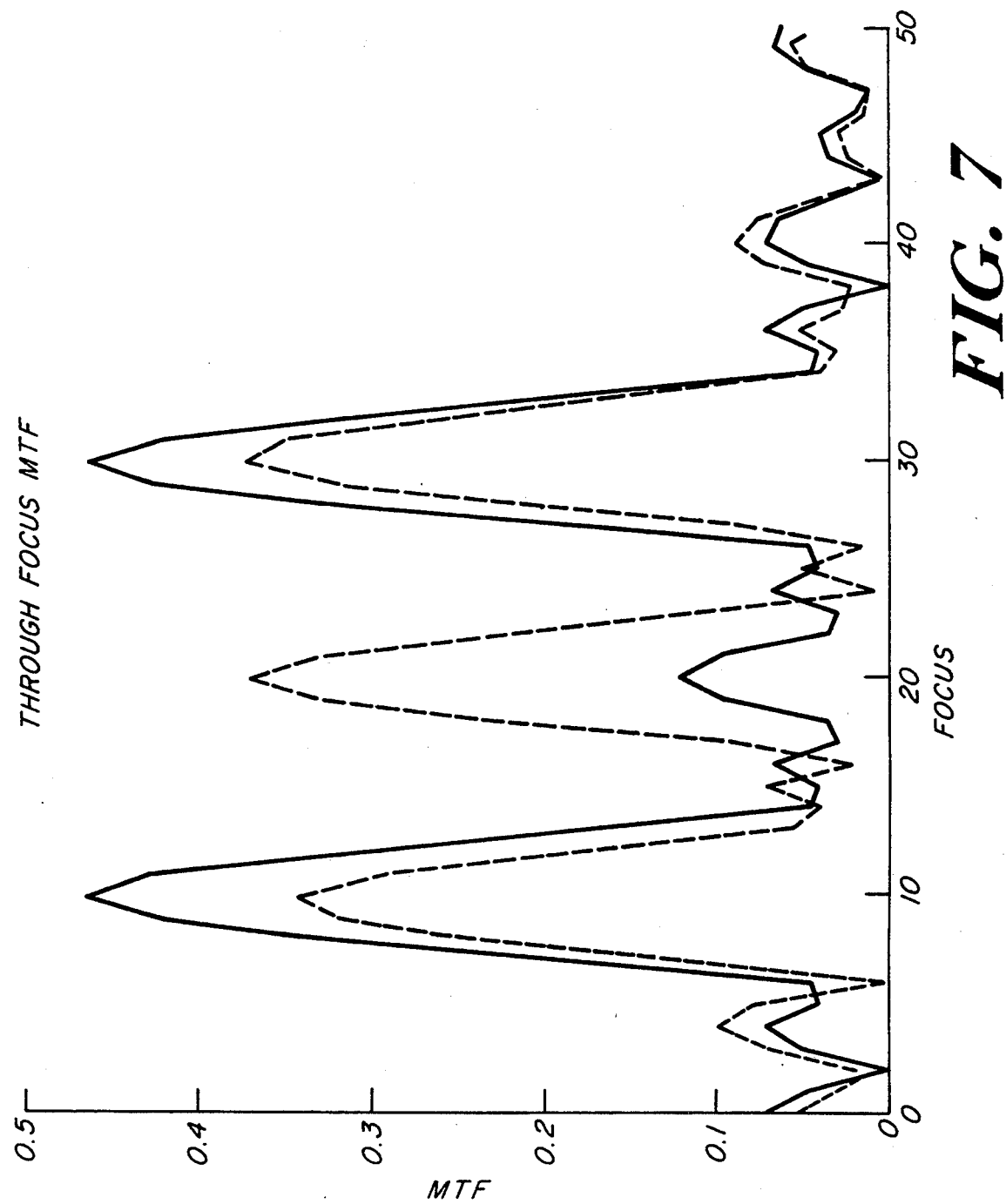
FIG. 7 is a plot of the MTF versus focus at a spatial frequency of one-tenth the diffraction limit. A comparison is shown of the trifocal IOL of the invention (dotted line), and the 3M design (solid line).

The MTF can also be plotted versus focus (i.e. image distance) at a given spatial frequency. FIG. 7 is a plot of the MTF versus focus at a spatial frequency of one-tenth the diffraction limit. Again, the solid line is the 3M design and the dotted line is the trifocal design. The peaks at 10, 20, and 30 represent the near, mid-range, and far vision respectively. Notice the dramatic improvement in the mid-range of the trifocal design over the 3M design.

Fabrication

A refractive/diffractive lens as described above with reference to FIG. 1 can be fabricated using a lithographic masking technique, generally as described in U.S. Pat. No. 4,895,790, hereby incorporated by reference. The technique as described therein is a multi-level masking technique for the purposes of producing a lens element having a diffractive lens profile with several different depths, or a grading of depths. As will be appreciated by those skilled in the art, the binary design of the trifocal lens requires only a single masking and etching step as the diffractive lens profile is of a single uniform depth. The protocol, briefly, is as follows.

Generally, with reference to FIG. 1, a binary phase profile lens body can be made from a material conventionally used in fabricating intraocular implants such as, for example, PMMA, by first for example using the lithographic masking technique to produce a master, then using the master as a plug to form a mold, and then using the mold to form the lens body. Alternatively, a laser writer could be used to first pattern the diffractive profile, and then the lithographic technique can be used to etch the diffractive surface to produce a master as above. This fabrication method produces a lens element that can have the desired profile shown such that the amount of incident light focused at each of $d_1$, $d_2$, and $d_3$ is 28.8%.

An intraocular lens implant can be made using a lens body having the configuration described above by providing fixation devices, preferably haptics, as are well known in the art. Or a one-piece lens having haptics provided as an integral part can be formed using standard fabrication methods combined with the lithographic masking technique.

Use

The overall dimensions and shape of the implant according to the invention are not materially different from those of known intraocular lens implants that are in common use. An implant according to the invention can be used instead of, or as a replacement for, a standard intraocular lens implant using known techniques of intraocular lens implantation.

What is claimed is:

1. An intraocular optical lens comprising a refractive component on an anterior surface of the lens, and a completely transparent diffractive component on a posterior surface of the lens, and a generally anterior-posterior optical axis, the diffractive component having a zero order, a negative first order, and a positive first order, the refractive component combined with the positive first order of the diffractive component adapted to focus the incident light on the lens for near vision, the refractive component adapted to focus the incident light on the lens for mid-range vision, and the refractive component combined with the negative first order of the diffractive component adapted to focus the incident light on the lens for far vision.

2. The lens of claim 1 wherein the diffractive component has a profile which is binary in phase.

3. The lens of claim 2 wherein said profile has a depth D given by $$D = \frac{0.32\lambda_0}{\Delta n}$$

where $\lambda_0$ is about 550 nm and $\Delta n$ is the difference between the index of refraction of the lens and the index of refraction of aqueous humor.

4. The lens of claim 2 wherein said profile radial transition locations, $r_m$, are given by $$r_m = \sqrt{\frac{m\lambda_0}{P}}$$

wherein $\lambda_0$ is a wavelength and
where m is 0, 1, 2, 3, ..., and P is the power of the diffractive element in diopters.

* * * * *